United States Patent
Stumpf et al.

(10) Patent No.: US 11,119,014 B2
(45) Date of Patent: Sep. 14, 2021

(54) SAMPLE PREPARATION AND SPECIFIC CAPTURE FOR MULTIPLEX DETECTION OF TARGET ANALYTES (I.E., BACTERIA, VIRUSES, ETC.)

(71) Applicant: Pathogen Systems, Inc., Broomfield, CO (US)

(72) Inventors: Curtis Hubert Stumpf, Kent, OH (US); Weidong Zhao, Kent, OH (US)

(73) Assignee: Pathogen Systems, Inc., Broomfield, CO (US)

(*) Notice: Subject to any disclaimer, the term of this patent is extended or adjusted under 35 U.S.C. 154(b) by 0 days.

(21) Appl. No.: 15/997,529

(22) Filed: Jun. 4, 2018

(65) Prior Publication Data

US 2018/0283997 A1 Oct. 4, 2018

Related U.S. Application Data (62) Division of application No. 15/064,403, filed on Mar. 8, 2016, now abandoned.

(60) Provisional application No. 62/132,232, filed on Mar. 12, 2015.

(51) Int. Cl.
| | |
|---|---|
| *G01N 33/543* | (2006.01) |
| *G01N 1/40* | (2006.01) |
| *C12Q 1/02* | (2006.01) |
| *G01N 35/00* | (2006.01) |

(52) U.S. Cl.
CPC .............. *G01N 1/405* (2013.01); *C12Q 1/02* (2013.01); *G01N 1/4077* (2013.01); *G01N 2001/4038* (2013.01); *G01N 2001/4083* (2013.01); *G01N 2001/4088* (2013.01); *G01N 2035/00564* (2013.01)

(58) Field of Classification Search
None
See application file for complete search history.

(56) References Cited

U.S. PATENT DOCUMENTS

| | | | | |
|---|---|---|---|---|
| 6,033,574 A | * | 3/2000 | Siddiqi | B03C 1/01 |
| | | | | 210/695 |
| 2004/0197833 A1 | * | 10/2004 | Loessner | C12N 9/503 |
| | | | | 435/7.2 |
| 2005/0013741 A1 | * | 1/2005 | a'Brassard | G01N 33/54326 |
| | | | | 210/695 |
| 2006/0252031 A1 | * | 11/2006 | Abbott | B82Y 30/00 |
| | | | | 435/5 |
| 2008/0182758 A1 | * | 7/2008 | Ugolin | C12Q 2545/114 |
| | | | | 506/9 |
| 2010/0144005 A1 | * | 6/2010 | Bin Kingombe | |
| | | | | G01N 33/56916 |
| | | | | 435/173.9 |
| 2015/0118688 A1 | * | 4/2015 | Weidemaier | B03C 1/01 |
| | | | | 435/7.1 |

OTHER PUBLICATIONS

Reidt et al., Automated Immunomagnetic Processing and Separation of Legionella pneumonphila With Manual Detection by Sandwich ELISA and PCR Amplification of the omps Gene, Innovation Brief, JALA Apr. 2011, pp. 157-164. (Year: 2011).*

* cited by examiner

*Primary Examiner* — Gary Counts
(74) *Attorney, Agent, or Firm* — Glenn H. Lenzen; Elevated IP, LLC (57) ABSTRACT

A method and apparatus for the rapid and reliable preparation of a sample for use in testing for target analytes such as bacteria, viruses, toxins and pathogenic agents in various products. A sample for testing the target analyte is collected from various sources. The method for sample preparation provides for an express process for preparing collected samples for testing. The collected sample may be concentrated by centrifugation, filtration, or other means suitable for sample concentration, homogenized with the addition of a broth and enriched for specified period of time. Immunomagnetic separation of the sample occurs with receptor-coated magnetic microspheres in different test-specific formulations (singleplex or multiplex). An automatic testing system is disclosed which includes a biological testing cassette, in which testing of the sample occurs using liquid crystal diagnostic methodologies.

13 Claims, 6 Drawing Sheets

SAMPLE PREPARATION AND SPECIFIC CAPTURE FOR MULTIPLEX DETECTION OF TARGET ANALYTES (I.E., BACTERIA, VIRUSES, ETC.)

CROSS-REFERENCE TO RELATED APPLICATIONS

This application is a divisional patent application of and claims priority to U.S. application Ser. No. 15/064,403, filed on Mar. 8, 2016, which claims priority to U.S. Provisional Patent Application No. 62/132,232 filed Mar. 12, 2015, the entire contents of which are incorporated herein by reference.

FIELD OF THE INVENTION

The present invention generally relates to sample preparation and capture of target analytes. More specifically, the present invention relates to sample preparation and receptor-based formulation for rapid detection and diagnosis of multiple target analytes/antigenic materials such as bacteria, viruses, toxins and various pathogenic materials.

BACKGROUND INFORMATION

Raw food material such as beef and produce, prepared foods such as ready to eat foods (RTE), dog food, and fruits, as well as food product production surfaces are often contaminated with significant numbers of microbes. Occasionally, sub-detectable numbers of analyte species, such as *Escherichia coli*(*E. coli*) O157:H7, non-O157 Shiga-toxin producing *E. coli*, *Salmonella* spp., *Listeria* spp., and others, co-contaminate these products and surfaces. Unsanitary preparation of these food products and unsanitary conditions in production areas can result in health problems. The United States Department of Agriculture (USDA) and United States Food and Drug Administration have imposed a zero tolerance policy for these and other hazardous analyte contaminants.

The normally low concentration of foodborne analytes necessitates enrichment (incubation and growth) of samples until the number of contaminating analyte reaches a detectable level. Because the number of non-analyte targets that exceeds the number of analyte targets is disproportionately large, the enrichment growth media must be designed to enhance analyte growth while suppressing the growth of non-analytes. Moreover, since the enrichment medium is specific to a bacteria strain, but not sample type, similar protocols are used to evaluate various food types of interest as well as surface/environmental samples.

The food industry generally examines three different areas (or critical control points) of food production: field product, the processing stage, and final product. Each of these critical control points involves different sample processing for captured analytes; food samples are directly mixed with a selective enrichment broth and homogenized, enriched for 4-48 hours, and detected using culture, immunologic, or molecular-based tests. Production facility sampling is done using a sponge or swab technique to collect samples from the surfaces of equipment and work areas. After enrichment, the liquid sample is recovered and processed for detection of analytes.

Recent contamination events in the meat, produce, pet food, and subsequent production facilities have led to a call for increased regulation of the overall production process. Rapid testing for harmful bacteria would greatly benefit the meat, produce, and pet food industries (as well as other manufacturing processes that prepare ingredients for consumption). Proactive responses to adverse testing results will decrease overall long-term costs and increase consumer confidence in food products. By way of example, the Crystal Diagnostics Xpress™ system is a rapid testing system, but still requires sample preparation before final diagnostics. (Crystal Diagnostics Xpress™ is a trademark of Crystal Diagnostics, Ltd.) The rapid and reliable method for sample preprocessing described herein further shortens the sample preparation time and maximizes the benefit of adopting this rapid testing method. In addition, a specific formulation of receptor-based detection and capture element combinations permits detection of multiple targets in a single test (i.e., multiplex testing). Using these unique receptor combination(s), multiple target analytes can be accurately and rapidly detected from the same sample.

In view of the above, it will be apparent to those skilled in the art from this disclosure that a need exists for an improved sample preparation and multiplex testing system and procedure for detection of analytes. This invention addresses this need as well as other needs, which will become apparent to those skilled in the art from this disclosure.

SUMMARY OF THE INVENTION

In accordance with an embodiment of the present invention, a method for preparing a test sample for the detection of antigen-containing target analytes is provided that comprises: homogenizing and enriching the sample with an enrichment media; adding either non-functionalized microspheres or functionalized receptor-conjugated magnetic microspheres and a solution to the sample to form a mixture; allowing the receptor to specifically bind to the exposed antigenic materials; precipitating the antigen-containing materials out of the mixture when the antigenic materials become specifically bound to the magnetic microspheres to form a precipitate and a supernatant; discarding the supernatant; and isolating the precipitate to produce a prepared sample. The prepared sample is then mixed with a diagnostic media, placed in a specifically prepared test cassette, and subjected to the detection procedure in the diagnostic platform.

In another embodiment, a method for development of a multiplex receptor-based system is also provided.

In yet another embodiment, a kit for preparing samples is provided comprised of magnetic microspheres, a sample plate, a magnetic holder and a test cassette. The magnetic microspheres are capable of specific binding to antigenic-containing materials contained within the samples. The magnetic holder can hold a plurality of samples, all of which may be processed simultaneously. The cassette contains a diagnostic media and is configured to hold the prepared sample.

These and other objects, features, aspects and advantages of the present invention will become apparent to those skilled in the art from the following detailed description, which, taken in conjunction with the accompanying figures, discloses a preferred embodiment of the present invention.

BRIEF DESCRIPTION OF THE DRAWINGS

FIG. 1.A. is an illustration of single antibody conjugated microspheres in accordance with an embodiment;

FIG. 1.B. is an illustration of the single antibody conjugated microspheres of FIG. 1A. added to a test sample containing a potential target material in accordance with an embodiment;

FIG. 1.C. is an illustration of the aggregates formed by the antibody conjugated microspheres after binding to a targeted material in accordance with an embodiment;

FIG. 3.A. is an illustration of multiple, antibody conjugated microspheres of different preselected formulations in accordance with an embodiment;

FIG. 3.B. is an illustration of multiple different antibody conjugated microspheres of FIG. 3.A. added to a test sample containing a potential target material in accordance with an embodiment;

FIG. 3.C. is an illustration of the aggregates formed by the multiple different antibody conjugated microspheres after binding to a targeted material in accordance with an embodiment;

FIG. 5.A. illustrates a format of a multiple antibody conjugated microsphere sample design having a first combination of antibody conjugated microspheres and a test sample distributed in a first panel of a multiplex microsphere test kit in accordance with an embodiment;

FIG. 5.B. illustrates a second panel of a multiplex microsphere test kit having a combination of antibody conjugated microspheres and a test sample distributed therein in accordance with an embodiment;

FIG. 5.C. illustrates a negative control panel of the multiplex microsphere test kit of FIGS. 5.A and 5.B in accordance with an embodiment.

DETAILED DESCRIPTION

Before proceeding with the detailed description, it is to be appreciated that the present teaching is by way of example only, not by limitation. The concepts herein are not limited to use or application with a specific type of apparatus, system or method for the detection of target analytes for rapid identification, diagnosis and treatment of contaminants in various materials. Thus, although the instrumentalities described herein are for the convenience of explanation, shown and described with respect to exemplary embodiments, it will be appreciated that the principles herein may be applied equally in other types of analyte detection apparatus, systems and methods without departing from the scope of the present invention.

Referring now to the drawings, the present invention comprises a method and an apparatus for preparation of a sample for use in testing for a wide range of harmful bacteria. A sample for testing analytes, such as *E. coli*O157: H7, non-O157 Shiga-toxin producing *E. coli, Salmonella* spp., or *Listeria* spp., is collected from various sources. The sources can include raw or cooked food, animal carcasses, pet food, or food production surface/environmental samples.

Figure 1A:
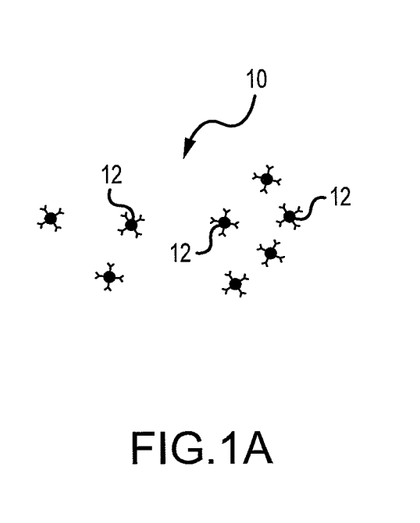
Figure 1B:
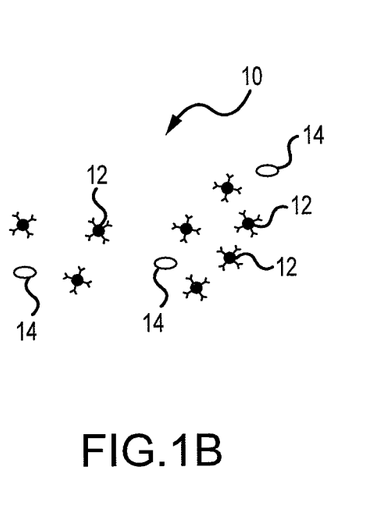
Figure 1C:
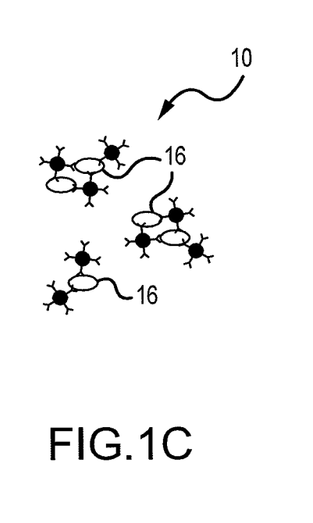
Figure 3A:
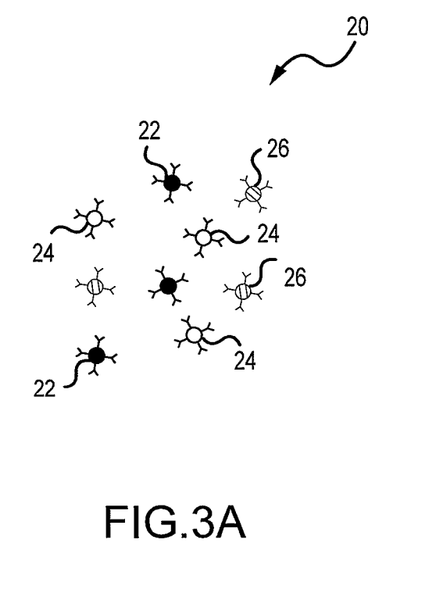
Figure 3B:
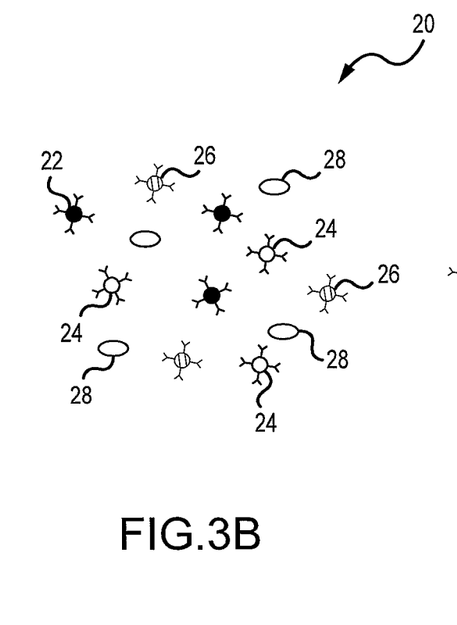
Figure 3C:
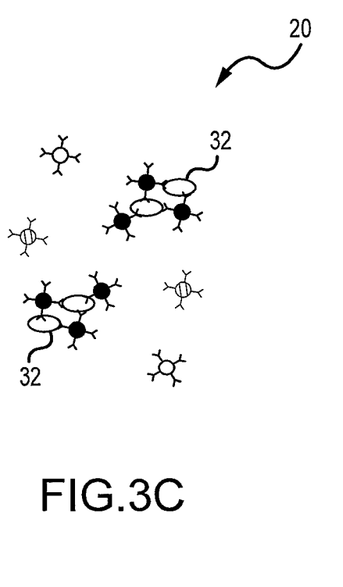

The method for sample preparation provides an expedited process for preparing collected samples for testing. Certain samples may be concentrated via centrifugation or filtration before or after enrichment. Samples are homogenized with a stomacher blender or mixed by hand agitation of the containment vessel with the addition of an enrichment broth. The samples are enriched using media at a temperature that is optimal for the specific target bacteria (e.g., 46° C. prewarmed media added to enrich *E. coli*O157:H7), and then placed in a warming device to maintain a constant, optimized growth temperature (typically 30-42° C.). Once enriched to an optimal time, immunomagnetic separation of the sample occurs with plain magnetic polymer beads or microspheres, such as non-functionalized plain polystyrene beads. Alternatively, functionalized polymer beads, such as carboxyl polymer beads or affinity ligands (receptor-coated) (e.g., antibody, aptamer, bacteriophage, etc.) magnetic microspheres of a specific size appropriate for detection in a detection system such as the Crystal Diagnostics Xpress™ system may be used. By way of example and not of limitation, the functionalized or coated magnetic microspheres may be streptavidin or latex coated magnetic polymer beads to which surface a receptor is then chemically conjugated to act as a receptor for the intended target analyte. The plain or receptor-coated magnetic microspheres may be formulated for a single analyte target, a singleplex format as shown in FIGS. 1.A, 1.B and 1.C, or combined into an advanced formulation for detection of multiple targets, a multiplex format as shown in FIGS. 3.A, 3.B and 3.C.

Figure 4:
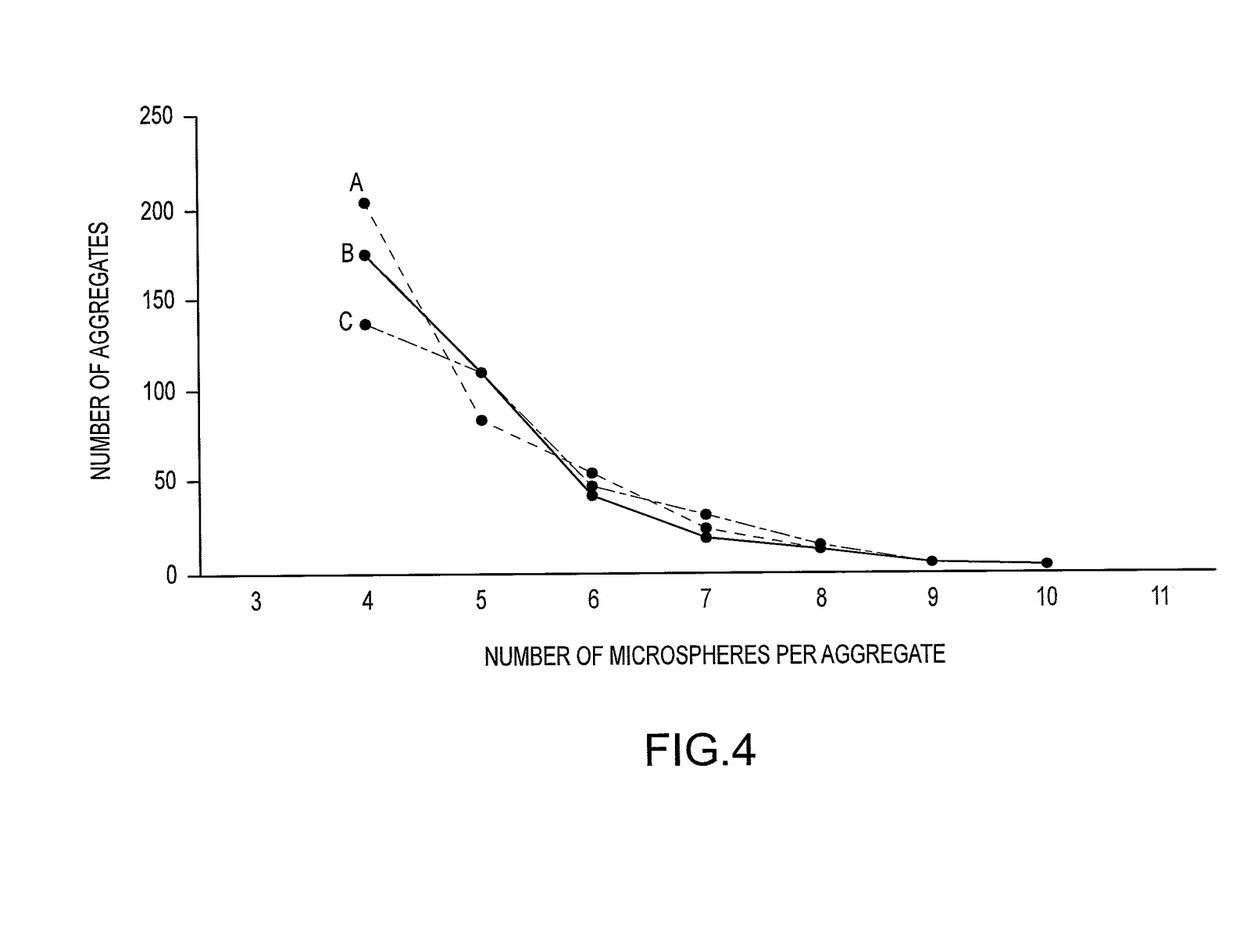
FIG. 4. is a graphical presentation of antibody detection of *Escherichia coli* O26 with one, two and three non-specific antibodies illustrating that the detection of an organism is not impeded by the combination of microspheres conjugated with different antibodies in accordance with the embodiments of the present invention.

It has been shown that the multiplex formulation of the receptor-coated magnetic microspheres does not impede the detection of the target analyte(s) as best illustrated by the antibody detection curves of FIG. 4). These curves plot the number of total aggregates (y-axis) vs. the number of microspheres per aggregate (x-axis) for the antibody detection of *Escherichia coli* O26 as a model organism under three different conditions: Plot A is the combination of *Escherichia coli* O26 antibody conjugated microspheres with two other non-specific antibody conjugated microspheres; Plot B is the combination of *Escherichia coli* O26 antibody conjugated microspheres with one other non-specific antibody conjugated microsphere; and Plot C is the *Escherichia coli* O26 antibody conjugated microspheres alone.

Returning again to the methodology of the instant invention, a biological testing cassette, in which testing of the sample will occur, is then prepared (or the receptor coated microspheres might be incorporated into the testing cassette). The cassette can be part of an automated testing system for testing of harmful bacteria in food, surface or environmental samples using the above-referenced platform, such as the microsphere test kit and its components shown in FIGS. 5.A, 5.B and 5.C and in FIG. 6. Examples of such automated testing systems are disclosed in U.S. patent application Ser. Nos. 12/373,051 and 12/398,144, both of which are hereby incorporated herein by reference.

Sample Collection

Food and surface/environmental samples from sources such as ground beef, produce (such as lettuce or spinach), pet food, food production surfaces and other environments can be collected for sample preparation according to the present invention. For example, in the case of testing ground beef for harmful bacteria, approximately 25-375 g of ground beef product is collected. In the case of testing a carcass, a food production surface, or an environment (e.g., machine (stainless steel), table (plastic), or floor (ceramic tile)), a sponge, swab or vacuum technique is utilized. After the sponge or swab contacts the surface, the sponge or swab is then directly enriched in an enrichment media, as will be described below in greater detail. Before or after sample enrichment, the sample can be concentrated by high-speed centrifugation or filtration to remove excess liquid. Up to approximately 500 ml of concentrated sample material, for example, can be used. Similarly, the sample from the carcass can be added to enrichment broth, and grown to detectable concentrations.

Enrichment

A range of 25-375 g of the collected sample is transferred into a sample bag for homogenization either using a stomacher or by hand mixing. Alternatively, a surface swab may be placed in a sample bag for mixing. The sample bag is preferably a filtered bag (e.g., from VWR International LLC or Nasco (Whirl-Pak®)), which includes a filter membrane dividing the inside thereof into two compartments. (Whirl-Pak® is a registered trademark of Nasco Sampling LLC.) Liquid can be extracted from the non-sample side of the compartment for division into aliquots. An enrichment broth (e.g., modified Trypticase™ Soy Broth plus Novobiocin (mTSB+n) for *E. coli* O157:H7) is added to the collected sample in the sample bag. (Trypticase™ is a trademark of Becton, Dickenson and Company. Novobiocin is the commercial trade name of an orally active antibiotic.) In this embodiment, approximately 1 to 3 (and as many as 10) times of pre-warmed (e.g., 42-46° C.) enrichment media is added to 1 part of the collected sample in the sample bag (wt/wt, vol/wt or vol/vol, e.g., approximately 1000 mL mTSB+n to 325 g of raw ground beef). The sample bag is then pummeled in the stomacher blender (or by hand) for approximately 30 sec. and then incubated at approximately 42° C. for approximately 9 hours (enrichment time is dependent on sample size and ranges from ~7 to ~24 hours for 25 to 325 g samples, respectively) in an incubator. After enrichment, up to 50 mL of the liquid fraction from the bag is poured out of the sample bag and into a sterile conical tube (or pipetted directly to the microspheres for processing). The conical tube is then capped and left undisturbed for approximately 5-10 min. A similar process is used for surface/environmental samples (though a smaller volume of media (approximately 10-50 mL) is added to the sample swab and it can be enriched in various types of containers).

Immunomagnetic Separation Materials

The present invention utilizes paramagnetic microspheres (from this point forward, simply described as magnetic microspheres) to prepare the sample for testing. Referring now to FIGS. 1.A.-1.C., a method and apparatus for the detection of a single analyte target, also referred to herein as a singleplex format or singleplex method and apparatus 10, specific for one target, is shown. In the singleplex format, a plurality of single antibody conjugated paramagnetic microspheres 12 in FIGS. 1.A and 1.B are prepared as described in greater detail below for the detection of a target material 14 (FIG. 1.B.). The magnetic microspheres may comprise iron, iron oxide, iron nitride, iron carbide, nickel and cobalt and mixtures and alloys thereof. In another embodiment, referred to herein as a multiplex format 20 depicted in FIGS. 3.A.-3.C., a plurality of magnetic microspheres, having different preselected formulations illustrated by exemplary, microspheres 22, 24 and 26, may be combined for detection of multiple analyte targets in the same sample.

Figure 2:
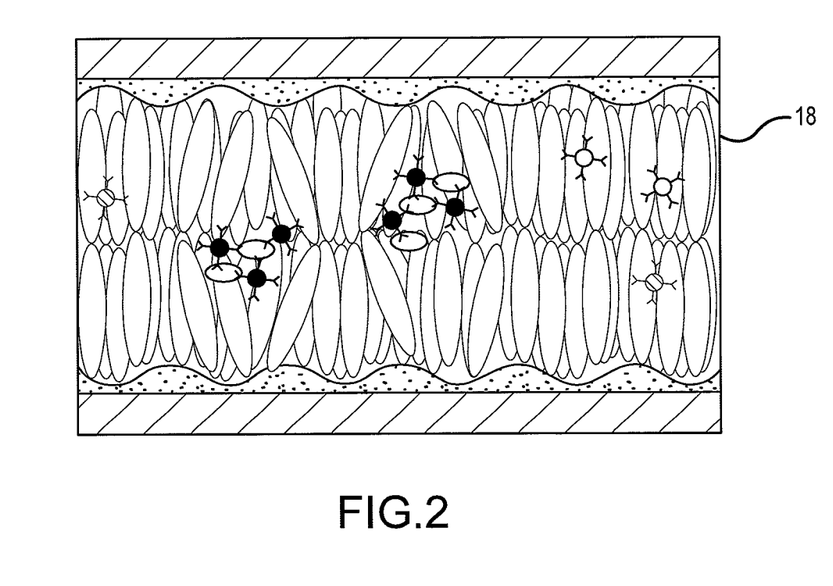
FIG. 2 is a top cross-sectional view of a liquid crystal detection medium for detecting aggregates formed by antibody conjugated microspheres after binding to a targeted material in accordance with an embodiment.

In the singleplex format, the magnetic microspheres 12 detect and bind to the single target 14 (for example, bacteria, a virus or a pathogen) to form an aggregate 16, as shown in FIG. 1.C. The aggregate may be dispersed into and detected in a liquid crystal medium 18, as best shown in FIG. 2. In the multiplex detection format, as shown in FIGS. 3.A, 3.B and 3C the magnetic microspheres 22, 24, and 26 combine with analyte targets 30 to form aggregates 32 (FIG. 3.C.). Dispersed in a liquid crystal medium 18 as discussed above with respect to the singleplex technique, the presence of aggregates 32 may be detected.

The magnetic microspheres may be prepared with a receptor (antibody, aptamer, etc.) in various ways. By way of example, and not of limitation, in an embodiment, approximately 100 to 200 µl of suspended antibody microsphere-mixture, is added to a deep well plate, as is known in the art. The concentration of microspheres may range from $1 \times 10^6$ to $1 \times 10^7$ per target depending on kit and application). Approximately, 100 to 200 µl of igG-conjugated (e.g., purified goat IgG from Jackson ImmunoResearch Laboratories Inc.) and blocked (e.g., with bovine serum albumin) magnetic microspheres may be used for the negative microsphere control. For example, the magnetic microspheres discussed herein can be Dynal microspheres from ThermoFisher Scientific (Waltham, Mass.), or other manufacturer's microspheres having similar properties.

Immunomagnetic Separation

Figure 5A:
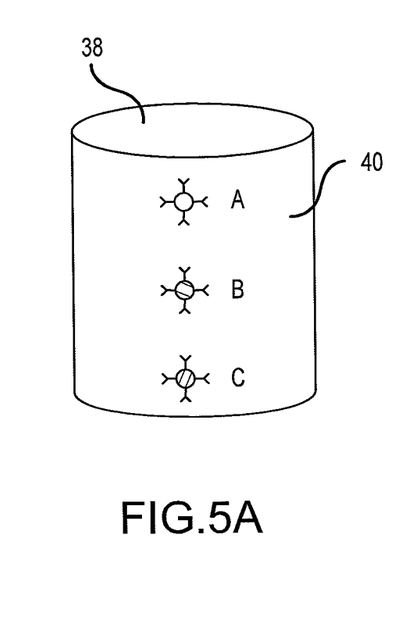
Figure 5B:
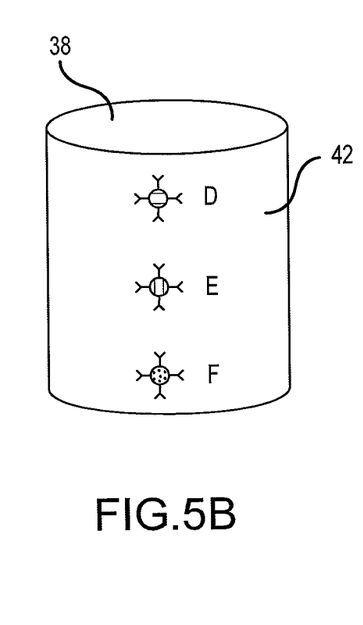
Figure 5C:
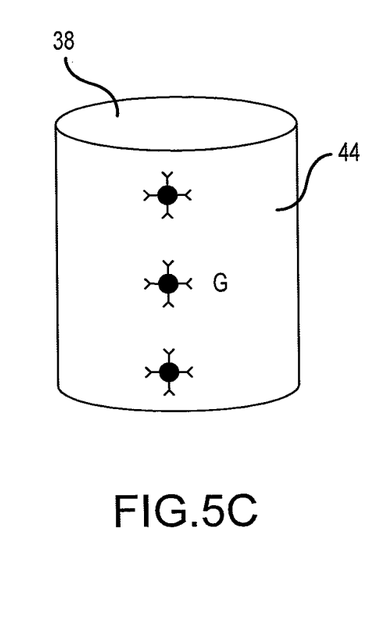

Using a pipette, for example, approximately 1-1.4 ml aliquots of supernatant (enriched collection sample) 38 are collected. For some sample types, collected aliquots can be centrifuged at 1000-5000×g for the optimal time (40-120 sec). As shown in FIGS. 5.A., 5.B and 5.C., approximately 100-600 µl of the supernatant is transferred to containers or receptacles 40, 42 and 44 in a deep-well plate (not shown). Preselected test antibody magnetic microspheres A, B and C are added to receptacle 40, (FIG. 5.A) and D, E and F are added to receptacle 42 (FIG. 5.B) respectively. Negative control antibody magnetic microspheres G are added to receptacle 44, as shown in FIG. 5.C. Alternatively, some sample types may require no centrifugation before addition to the antibody magnetic microspheres.

The deep-well plate with the enriched collection sample and magnetic microspheres is incubated on a microplate vortex mixer for approximately 5-30 min. at room temperature and at a slow mixing speed. The mixer may be a microplate vortex mixer from Thermo Scientific, Inc., for example.

The deep-well plate is then transferred to a 96-well plate bar magnet (e.g., V&P Scientific) for approximately 3 min. to permit the microspheres to be captured from the sample matrix. While the magnetic microspheres remain held at the inner wall by the magnet, the liquid in the deep-well plate is removed by a pipetting and replaced with 1000 µl of wash buffer such as phosphate buffered saline (PBS) or PBST, i.e., PBS with Tween-20® (0.01-0.03%), a polyoxyethylene sorbitol ester available from Sigma Aldrich, for example. (Tween-20® is a registered trademark of Croda International PLC.)

The deep-well plate remains on the magnet and is permitted to rest for approximately 2 minutes, before the supernatant is again removed while the microspheres are retained. Alternatively and depending on the sample matrix and the background microflora, the deep-well plate may be returned to the mixer for additional mixing with the wash buffer, or multiple exchanges of wash buffer may be incorporated.

After final collection of the magnetic microspheres on the magnet and removal of the entire volume of wash buffer, the deep-well plate is then removed from the magnet and the microspheres are resuspended in an appropriate volume (e.g., 20-100 µl) depending on the desired concentration.

The sample is then transferred to appropriate strip microtubes or microplates for mixing with the detection medium for analysis.

Preparation for Crystal Diagnostics

Liquid crystal with a buffer solution (MilliQ® water, Sterile DNA/RNA quality water, or similar) is mixed (vortexed) and allowed to rest for a prescribed period of time (e.g. 20 min) at 60° C. until fully dissolved. (MilliQ® is a registered trademark of Millipore Sigma.) Then, the temperature of the liquid crystal in suspension is lowered to 40-45° C. Thereafter, it is ready for mixing with the magnetic microspheres. Approximately 20-100 µl (±5 µl) of the solution is aliquoted to a separate 200 µl tube, for example.

The immunomagnetic separated sample (washed magnetic microspheres), prepared as described above, is briefly mixed using pipette mixing to homogenize the sample and re-suspend the microspheres. Approximately 4-20 µl of the sample is then added to the 20-100 µl, respectively, of liquid crystal and buffer solution and pipette mixed.

Figure 6:
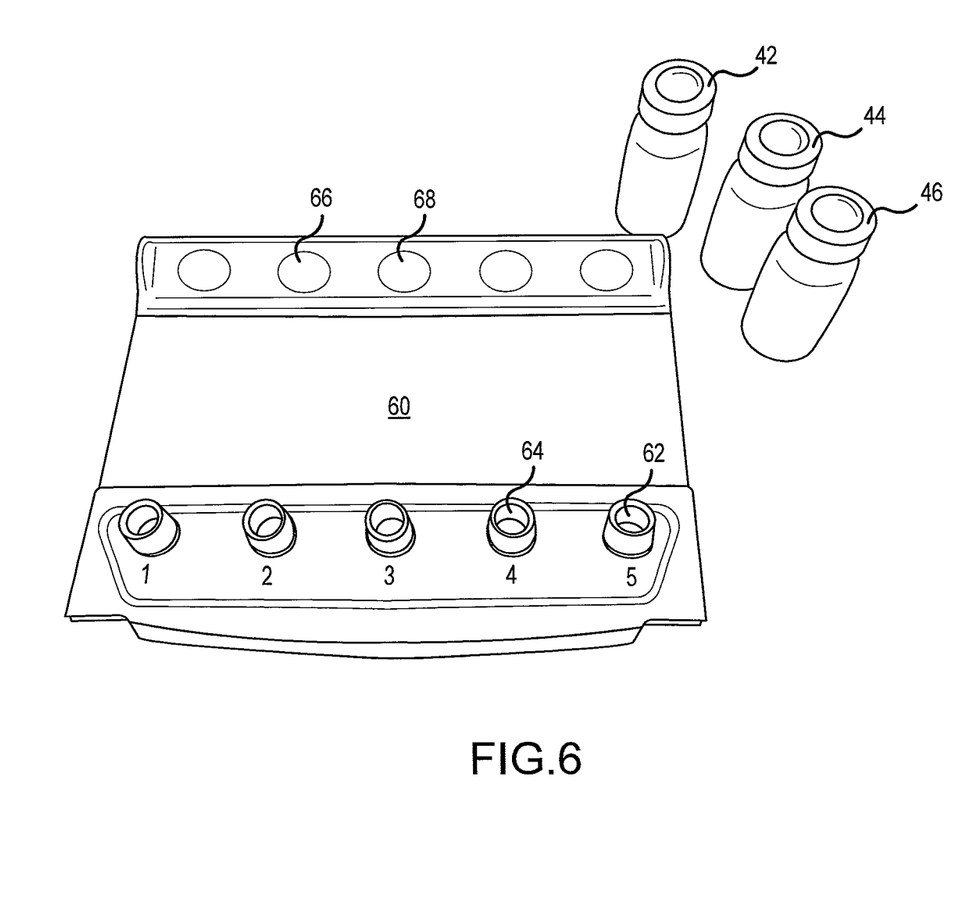
FIG. 6 is an example of a multiplex antibody conjugated test kit showing a bio-cassette and test sample containers in accordance with an embodiment.

As shown generally in FIG. 6, a cassette 60 is used to detect the analyte. The cassette includes a plurality of separate, mateable housings 62, forming multiple reservoirs 64 with respective inlets for receiving the sample. A second portion of the cassette includes multiple channels 66 with inlets 68 for receiving the sample, which are operatively connected to the receiving inlets. Specifically, each of the inlets is tapered so as to fit within the inlet of the other mateable housing, which forms a concave cavity sized and configured to receive the first inlet. Approximately 50 µl of the liquid crystal-sample mixture is loaded into each reservoir desired for use.

The cassette is then inserted into a crystal diagnostic device, such as The Crystal Diagnostic Xpress™ Reader (not shown), containing a liquid crystal medium such as medium 18 illustrated in FIG. 2, to detect any analyte which may be in the sample using the diagnosis medium by methods described in U.S. patent application Ser. Nos. 12/373,051 and 12/398,144, for example.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

It will be apparent to those skilled in the art from this disclosure that various changes and modifications can be made herein without departing from the scope of the invention as defined in the appended claims. Furthermore, the foregoing descriptions are provided for illustration only, and not for the purpose of limiting the invention as defined by the appended claims and their equivalents.

What is claimed is:

1. A method for preparing a sample containing multiple target analytes of antigenic materials collected from a source for detection of the analytes in a liquid crystal detection medium, the method comprising:
   collecting the sample from the source;
   placing the sample in a containment vessel;
   selecting enrichment media or broth adapted to enrich the target analytes in the sample;
   determining an enrichment media temperature at which the growth of the target analytes are optimized;
   prewarming the enrichment media to the optimized growth temperature;
   adding a preselected quantity of the prewarmed enrichment media to the sample in the containment vessel;
   homogenizing the sample and the enrichment media in the containment vessel whereby a homogenized sample-enrichment media mixture is formed;
   transferring the homogenized sample-enrichment media mixture to a warming device;
   maintaining the homogenized sample-enrichment media mixture at a constant, optimized growth temperature for a preselected optimal enrichment or incubation time period, whereby a precipitate and a supernatant are formed;
   collecting the precipitate and the supernatant into separate sterile containers;
   capping each of the sterile containers and leaving the sterile containers undisturbed for a preselected period of time, whereby enriched collection samples are formed therein;
   transferring a quantity of each of the enriched collection samples to one or more receptacles;
   adding a preselected quantity of paramagnetic microspheres having different preselected formulations to each of the one or more receptacles, each of the paramagnetic microspheres being adapted to bind to preselected antigenic materials contained within each of the samples;
   incubating the enriched collection samples and paramagnetic microspheres at a preselected temperature for a preselected period of time, whereby a sample matrix is formed;
   applying a magnetic field to the matrix for a preselected period of time, whereby the paramagnetic microspheres bound to an antigenic material are separated from the sample;
   removing any supernatant remaining in each of the one or more receptacles;
   washing the paramagnetic microspheres with a phosphate buffered saline solution (PBS) or with a phosphate buffered saline with a polyoxyethyene sorbitol ester (Tween-20®) (PBST) forming a mixture;
   letting the mixture sit undisturbed for a preselected period of time;
   removing any supernatant remaining in the receptacle;
   removing the magnetic field and resuspending the paramagnetic microspheres in a preselected volume of a buffer solution; and mixing the paramagnetic microspheres and buffer solution with a preselected volume of a liquid crystal detection medium.

2. The method of claim 1 further including the step of concentrating the sample via centrifugation or filtering before the step of enrichment.

3. The method of claim 1 further including the step of concentrating the sample via centrifugation or filtering after the step of enrichment.

4. The method of claim 1 wherein a concentration of resuspended paramagnetic microspheres in the preselected volume of buffer solution is in a range of $1 \times 10^6$ to $1 \times 10^7$ per target analyte.

5. The method of claim 1, wherein the mixture further comprises a surfactant.

6. The method of claim 5, wherein the surfactant is a nonionic surfactant.

7. The method of claim 1, wherein the paramagnetic microspheres are comprised of a material selected from the group consisting of iron, iron oxide, iron nitride, iron carbide, nickel and cobalt, and mixtures and alloys thereof.

8. The method of claim 1, wherein the paramagnetic microspheres are magnetic polystyrene beads.

9. The method of claim 1, wherein the paramagnetic microspheres have an average diameter within the range of approximately 0.1 μm to approximately 100 μm.

10. The method of claim 9, wherein the paramagnetic microspheres have an average diameter within the range of approximately 1 μm to approximately 50 μm.

11. The method of claim 1, wherein the paramagnetic microspheres have an average diameter within the range of approximately 1 μm to approximately 5 μm.

12. The method of claim 1, wherein the antigenic materials are selected from the group consisting of immunoglobulins, proteins, lipo polysaccharides, or enzymes.

13. The method of claim 1, wherein the sample is a meat, produce, pet food, a sample collected from a surface, or a fecal sample.

* * * * *